United States Patent [19]

Buttazzoni

[11] Patent Number: 4,544,599
[45] Date of Patent: Oct. 1, 1985

[54] ELASTICALLY DEFORMABLE ARTICLES OF CARBON FIBERS, AND METHOD FOR PRODUCING THE SAME

[75] Inventor: Bernard Buttazzoni, Marseilles, France

[73] Assignee: Societe Europeenne de Propulsion, Puteaux, France

[21] Appl. No.: 615,137

[22] Filed: May 30, 1984

Related U.S. Application Data

[63] Continuation-in-part of Ser. No. 463,162, Feb. 2, 1983, abandoned.

[30] Foreign Application Priority Data

Feb. 9, 1982 [FR] France ................... 82 02094

[51] Int. Cl.[4] ............................................. B32B 7/00
[52] U.S. Cl. .......................................... 428/262; 427/2; 427/249; 428/408
[58] Field of Search ............... 427/2, 173, 174, 176, 427/175, 249, 275, 276; 156/173, 175; 264/81; 428/262, 408

[56] References Cited

U.S. PATENT DOCUMENTS

| 3,369,920 | 2/1968 | Bourdeau et al. | 427/249 |
| 3,410,746 | 11/1968 | Turkat et al. | 427/249 |
| 3,531,249 | 9/1970 | Turkat | 264/81 |
| 3,657,404 | 4/1972 | Ettinger | 264/81 |
| 3,715,253 | 2/1973 | Olcott | 427/249 |
| 3,895,084 | 7/1975 | Bauer | 264/81 |
| 3,944,686 | 3/1976 | Froberg | 427/249 |
| 3,949,106 | 4/1976 | Araki et al. | 427/249 |
| 3,991,248 | 11/1976 | Bauer | 427/249 |
| 4,178,413 | 12/1979 | DeMunda | 427/249 |
| 4,318,948 | 3/1982 | Hodgson | 264/81 |
| 4,397,901 | 8/1983 | Warren | 427/249 |

*Primary Examiner*—Sadie L. Childs
*Attorney, Agent, or Firm*—Arthur B. Colvin

[57] ABSTRACT

The present invention relates to a method for producing elastically deformable articles constituted of a textile substrate of carbon fibers which are elastically deformable with respect to an at rest shape, wherein a flexible structure of carbon fibers is used, a predetermined form being set for this textile by means of shaping tools, and said textile being retained in said at rest shape by forming around the said fibers a thin coating of rough laminar pyrolytic carbon deposited by chemical vapor infiltration at high temperature without bonding of the fibers one to another. The textile can be given a flat form by using holding plates. It is possible to start from a braided sleeve which is either compressed or stretched axially around a mandrel. It is also possible to use a woven tape which is wound in a conical pseudo-spiral for use as a cardiac valve.

11 Claims, 11 Drawing Figures

ELASTICALLY DEFORMABLE ARTICLES OF CARBON FIBERS, AND METHOD FOR PRODUCING THE SAME

This application is a continuation-in-part of application Ser. No. 463,162, filed Feb. 2, 1983, and now abandoned.

BACKGROUND OF THE INVENTION

The present invention relates to a novel kind of elastically deformable articles constituted of walls which are elastically deformable with respect to a balanced form, and to a method for producing the same.

By wall is meant a physical body substantially corresponding to a mathematical surface, either developable or not. The thickness of the wall is mathematically negligible as compared to its extension. Thus, the articles concerned by the invention can be in the form of plane or skew tubular pipes; conical, spherical, toroidal, helicoidal surfaces or any other complex surface.

By balanced form of an elastically deformable object is meant the original shape of this article, to which the article tends to return after having been stretched, compressed, or deformed. In other words, balanced form refers to the rest condition of an elastically deformable article.

Manufactured articles of this kind already exist for various purposes and are used in numerous fields of technology or even of everyday life.

For example, certain applications such as hydraulic applications, require flexible and strectchable tubes or conduits, designed to be fixed by their two ends to two endpieces, the respective position of which is variable in space within set limits, while allowing an unperturbed flow of fluid in any position adopted by said endpieces.

Numerous devices are sold on the market, either in plastic or rubber-based tubular form, or in the form of textiles woven or braided from polymers, which textiles can be reinforced by a sheathed metallic reinforcement.

Unfortunately, these conduits are often not longitudinally extensible and do not tolerate being misaligned or being bent too sharply without being crushed or damaged.

Their resistance to temperature is limited to that of their constituting materials, and consequently does not exceed a few hundred degrees, which is not sufficient for a number of applications.

On the other hand, elastically deformable articles of the above-mentionned kind also exist in nature: a number of blood vessels, organic membranes or cartilaginous tissues are indeed constituted by elastically deformable walls. In some surgical operations, it is necessary to replace those natural elastically deformable organs by artificial prosthesis, but until now no substitution article has been actually satisfactory from the double point of view of elasticity and biocompability.

One object of the invention is to provide a new type of articles constituted of elastically deformable walls with improved qualities that can find useful applications in the field of surgery as well as in the field of industry when hard environmental conditions of temperature, oxidation, etc. are met. The invention is, of course, not limited to such applications, but those appear to be exceedingly important at the present time.

SUMMARY OF THE INVENTION

The method according to the invention for producing such articles, uses a flexible textile substrate of carbon fibers, constituted of flexible walls. Said textile is given by means of appropriate shaping tools, the form intended to be the balanced form of the finished article, and is "locked" in that balanced form by providing around the fibers a very thin covering of rough laminar pyrolytic carbon by chemical vapor pyrolytic treatment. The formation of the very thin film around each fiber of the textile is such that on the one hand it enables the finished article, once freed from the shaping tool, to keep the imposed balanced form in absence of any deforming stress, and on the other hand, it confers the whole an elasticity which enables the structure to be deformed under a stress of some kind and to return to its balanced form in the rest position by elastic return, once the stress is suppressed. In other words, and in contradistinction with all the known pyrolytic treatments, the "locking" phase does not lock the textile definitively in a completely rigid position, but it "memorizes" an elastic form, from which the article can be deviated by external forces and to which it automatically returns by internal elasticity.

BRIEF DESCRIPTION OF THE DRAWINGS

The invention will be more readily understood on reading the following description with reference to the accompanying drawing, in which.

DETAILED DESCRIPTION

Figure 1:
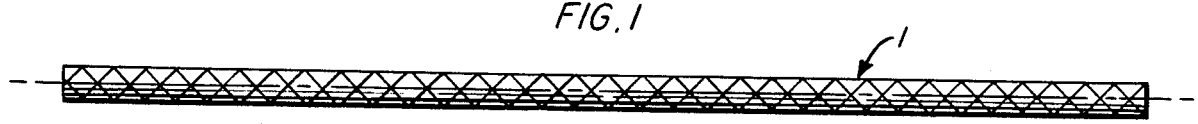
FIG. 1 shows a sleeve of braided fibers before treatment.

The starting flexible textile of carbon fiber must be capable of important reversible deformations.

The elementary fibers or filaments are preferably chosen amongst continuous carbon fibers having a diameter comprised between 7 and 10 microns. They are aligned side by side, by groups of 500 to 10000 filaments constituting flat roves, the thickness of which must not exceed ten diameters of fiber, its width depending on the number of filaments.

The elementary fibers are such that they can be bent under a minimum radius of curvature equalling ten fiber diameters without breaking.

The textile is produced by any conventional textile means (weaving, braiding, knitting, felting, needling, etc.) using roves to form a web, a satin, a flat braid, a tubular braid, etc., with a mono-layer wall.

The rove arrangement of the textile can be such as to leave a clearance between neighbouring roves in order to permit the shaping of the textile into a geometrical surface which cannot be developed (sphere, tore, . . . ), by relative sliding of the criss-crossed roves of the textile. These clearances are not necessary for obtaining developable surfaces (cylinders, cones, . . . ).

The angular orientation of the roves in the textile is chosen in order that the textile can be lengthened or shortened, in the direction of its extension, due to the angular variation of this orientation: opening of the angle formed by two crossing roves in order to reduce the distance of two points located on the bisectrix of this angle and, conversely, shutting of this angle to increase the distance of these two points.

The chemical treatment of the invention consists in grafting on each elementary fiber of the textile a sheath of pyrolytic carbon having a microstructure of the rough laminar type, so that this sheath can follow the same deformations as the elementary fiber without breaking. The thickness of the sheath does not exceed 1.5 micron.

The known processes for producing coating of pyrolytic carbon are generally carried out up to a point where the obtained coating is too thick and involves either the simultaneous breaking of both the fiber and the coating under bending, or peeling off of the coating under deformation. Even in the case of known processes leading to relatively thin coatings of pyrolytic carbon, no provision has been made heretofore to ensure that this coating had a rough laminar microstructure, which is an essential point for obtaining that this coating be elastic and follow the fiber deformation without breaking. It must be borne in mind that in the known processes, vapor-deposition of pyrolytic was used to bond and harden a fibrous material.

The surface treatment according to the invention "freezes" each elementary fiber in its position imposed by the shaping tools and permits the fiber to be deformed by stress, once out of the tools, in such a way that:

either the rectilinear shape of the treated elementary fiber can be bent under a curvature radius of at least ten fiber diameters, or the curved shape of the treated elementary fiber can be straightened up to a rectilinear shape, and that the fiber resumes its original balanced shape after suppression of the deforming stress.

The treatment according to the invention, hereinafter called pyrocarbon stiffening, does not bond the fibers constituting a rove with one another, and does not bond either the roves with one another at their crossing point, this permitting relative displacements of the fibers and of the roves under important deformations of the treated article. This treatment also implies that the density of the treated article is not increased with regard to that of the starting textile.

As for the tool used to give to the textile the predetermined balanced form, it must be designed to permit the above described surface treatment. To this effect, the tool is designed to maintain the textile while minimizing the contact surfaces between the textile and the tool: thus the textile is well exposed to the treatment fluids without useless mask.

The shaping tool is preferably constituted by a grooved or perforated polycrystalline graphite material, or by a light lattice of meshes of carbon fibers. After that the tool has been given its definite form, it is covered with pyrolytic carbon in order to prevent the textile from adhering to the tool during the "stiffening" treatment. In fact, experience has shown that the intimate contact of the virgin textile with the pyrocarbon of the shaping tool surface does not lead to a bridging by a pyrolytic structure, but that the latter grows preferentially on the virgin textile.

FIGS. 1 to 7 illustrate enbodiments of vascular ducts in carbon fibers which have optimum properties of hemocompatibility.

FIG. 1 shows a sleeve 1 braided with 32 roves of 1000 filaments over an inner diameter of 3 mm. The length of sheath measures 120 mm before any treatment.

In order to give it, by compression, the required balanced form, the sleeve is placed over a mandrel 2 in graphite, which is partly threaded at least at its two ends to screw on supporting nuts 3 permitting to adjust the selected rate of compression.

Figure 2:
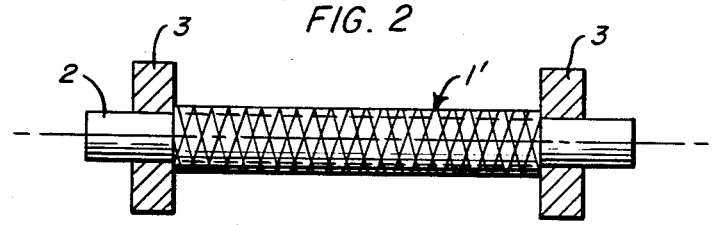
FIGS. 2 and 3 show how the textile of FIG. 1 is held in its balanced form, according to two embodiments corresponding to different rates of compression of the textile.
Figure 3:
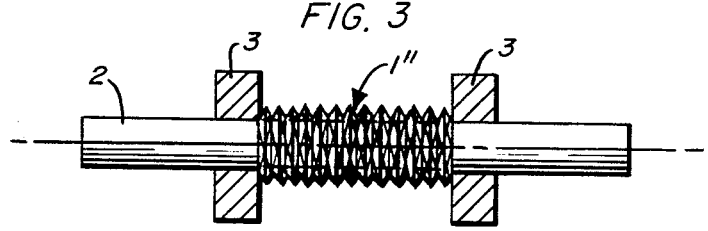

According to FIG. 2, the sleeve is compressed by one-third (ratio of compressed length to initial length) on a diameter of 5 mm.

Said compressed form is "fixed" by chemical vapor infiltration of pyrocarbon at high temperature. The precise conditions of temperature will be considered later.

The proportioning of the treatment is studied in order to obtain around each elementary carbon filament (of about 8 micron in diameter) a pyrocarbon film of thickness less than 1 micron. Said pyrocarbon film fixes each filament in the position in which the equipment holds it, and gives it greater or lesser flexibility, depending on its thickness.

Once removed from its mandrel (FIG. 4), the tube 1' retains the form imposed by the equipment, but it is capable of withstanding wide ranges of deformations and of returning to its balanced form without any alteration.

Figure 4:
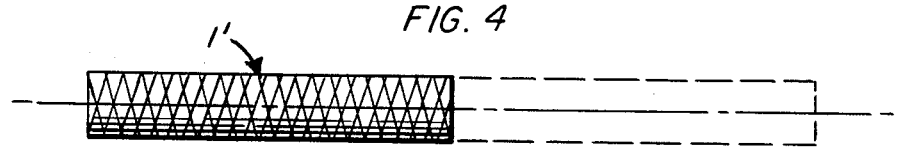
FIGS. 4 and 5 show the textiles of FIGS. 2 and 3 in the rest position (in block lines) and stretched under a force of 100 g (in dotted lines)

FIG. 4 shows the free tube with joining spires which is obtained, the longitudinal stretchability of which varies depending on the treatment, and can reach for example a stretchability of 120% under a force of 100 g.

For a stretching of 100%, the diametral shrinking is 25%. The crushing pressure is about 0.5 bar. This free and supple tube is insensitive to the crushing or bending effect under small radii of curvature (going up to R'=twice the diameter, FIG. 6) or under a twisting deformation.

Figure 5:
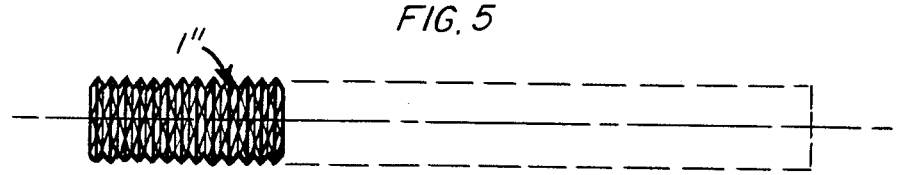
Figure 6:
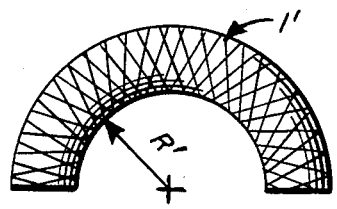
FIGS. 6 and 7 show the textiles of FIGS. 2 and 3 in a bent position.
Figure 7:
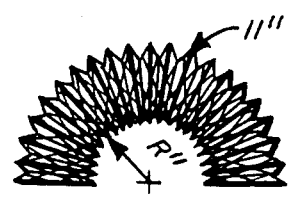

When selecting a compression rate of 1/6 (FIG. 3) the braided textile even "buckles", and an accordeon-pleated tube 1" is obtained, whose axial stretching rigidity is even less (for example 300% stretching under a pressure of 100 g, FIG. 5). When the stretching reaches 100%, the diametral shrinking is 20% and the crushing pressure is more than 1 bar. The tube can stand being curved without crushing, with a radius of curvature R" equal to the diameter of the tube.

One advantage of the method according to the invention in vascular surgery is to be able to obtain, with pure carbon, flexible tubes which cannot be produced by direct weaving or knitting, either with polymer textiles, or with carbon fibers.

The production method is applicable to any diameters of the sleeve and to geometrical forms which are not necessarily volumes of revolution. It is thus possible to obtain conduits of 16 mm diameter for tracheal prosthesis with a flat piece. The edges of the prosthesis are prevented from fraying by turning over the ends of the sleeve.

According to another particularly advantageous embodiment, it is possible to produce nonreturn valves, such as for example cardiac valves.

Figure 8:
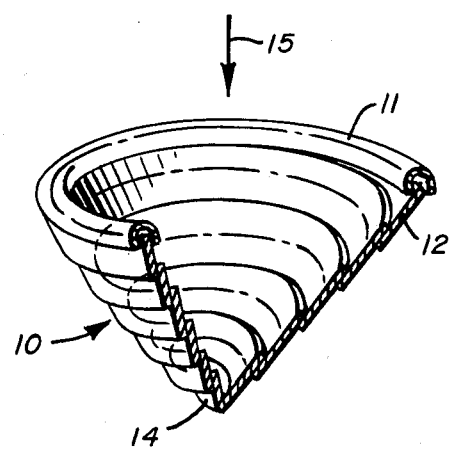
FIGS. 8 and 9 show another embodiment of a textile according to the invention, as a cardiac valve, respectively closed in its rest position and open under the effect of a flow.

FIG. 8 shows a non-return valve 10 in the rest position, which valve comprises a rim 11 inside which a continuous flexible tape 12 is wound in successive truncated spires.

In this rest position, the tape forms a tight pseudo-membrane, of conical shape with, in one precise embodiment, a diameter of 25 mm at the base, and a height of 18 mm, the rim itself being 5 mm high.

Each truncated spire partly overlaps the preceding one which is internal thereto. Said overlapping is achieved from the base of the cone to its apex by the smaller spire resting on the next one and so on, starting the winding with the central spire 14 which is cone-shaped (to ensure tightness at that level). Said cone may be provided with a calibrated orifice for a controlled return flow.

The valve 10 keeps the closed position shown in FIG. 8 as long as the difference in fluid pressure is experienced in the direction of arrow 15, or else when this pressure difference is nil.

Figure 9:
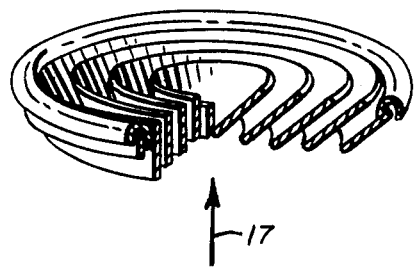

When the difference in fluid pressure is experienced in the other way, as illustrated by arrow 17 in FIG. 9, the valve 10 passes, under the effect of this pressure, to a second position from an equilibrium between the force which elastically returns the spire of tape towards the first position and the force exerted by the dynamic pressure of the fluid.

In order to form said valve, the pseudospiral generating tape is:
  either cut from a flat portion of the textile,
  or obtained directly by special flat helical weaving of gradually increasing diameter,
  or constructed from angular sectors previously cut flat, and joined together according to a generating line, the assembly constituting the preceding spiral.

The shaping of the conica pseudo-spiral is carried out on a cone-shaped equipment starting with the solid cone-shaped center. The developed form and the angle of the cone are adapted so that, once the winding is completed, the generating lines of the spires, at the place where they are overlapped, are parallel.

The shaping of the circular rim presents no particular difficulty when, here again, using a hemmed tape of carbon material bent to the desired diameter by way of a special tool equipment.

The rim is joined on to the cone by placing the last spire in such a way that it overlaps on the inner hem, as shown in FIG. 8. The two elements can be joined together by doing a seam with a carbon thread or by carbon sealing.

The material is thereafter treated with pyrocarbon to give it the desired elastic rigidity: an adequate refractory tool or a temporary seam with a thread in a material which dissolves at high temperature enables to keep the pseudo-spiral in the closed position, the spires being in contact where they overlap.

This treatment is conducted at high temperature (900° C.) by chemical vapor infiltration of pyrocarbon into the actual weft of the texture. This carbon "stiffening" associated to the very nature of the carbon fibers, fixes the pseudo-spiral in a stable rest position which, immediately attempts are made to move it from that position by axial displacement of the top towards the base, initiates a return force induced by the bending/twisting stress which occurs immediately in the normal cross-section of the spiral tape.

The performances of such a valve are up to the conditions of operation of a natural valve. In one special embodiment, the following characteristics have been measured:
  resistance of the pseudo-spiral to the return pressure: over 250 mm Hg specified value for biological valves,
  opening overpressure less than 10 mm Hg specified,
  leaks with untreated valve: 20 cm3/s of water under 25 mm Hg,
  Flow rate when valve fully opened: more than 500 cm3/s of water under 25 mm Hg,
  complete displacement of the top under full flow: 20 mm,
  actual frequency in the air: substantially equal to 10 Hz,
  mass of the spiral: 0.4 g and diameter 25 mm,
  great resistance to stress as long as the deformations remain average.

The prior encasing of the valve just before implantation, is effected according to the known method of proofing the textile of the spires by pre-operative blood coagulation.

The implantation consists in inserting in the right way the conical valve equipped with its rim, perpendicularly in the aortic duct regardless of the angular orientation, and then stitching up the stitches of material constituting the rim with the vascular wall at the required place.

Operation under normal heart circulation relies on the property of the carbon materials to become covered with a neo-tissue of at the most 100 microns of final thickness after two months when the textile is washed with the blood flow. Said neo-tissue completes the proofing of the textile and creates a homogeneous state of surface ensuring tightness where the spires overlap. The permanent throbbing of the spires with a clearance of more than 3 mm prevents the formation of thrombosis.

Furthermore, a tissular colonization occurs at the level of the rim against the vascular wall.

Figure 10:
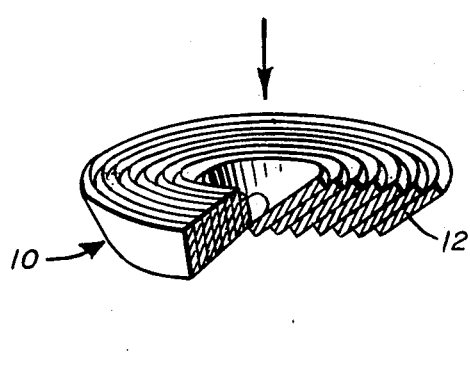
FIGS. 10 and 11 show a variant of the cardiac valve of FIGS. 8 and 9.
Figure 11:
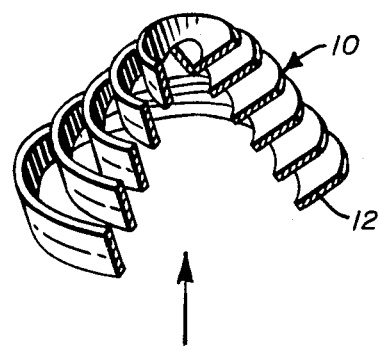

Dependng on the type of valve—mitral or tricuspid—different designs may be necessary. A variant can be obtained from a flat form in the rest position (FIGS. 10 and 11) therefore less voluminous in the upstream direction (also known as "flat" valve).

In this case the truncated spires, of gradually increasing or constant width, entirely overlap one another so that their upstream and/or downstream edge remains inside the same plane when the valve is in the rest position.

Another application of the invention in cardiac valves consists in using a tubular form in carbon material, the edge of which is gathered to form three lips, the elasticity of which lips is ensured by a treatment with pyrocarbon.

Another application of the method according to the invention to a sleeve-shaped textile is possible by holding the sleeve stretched on its mandrel: the resulting braid thus offering a high stretching rigidity and becoming a tendinous or ligamentous reinforcement with an elasticity of 10% until breakage instead of a nil elasticity with only longitudinal fibers.

According to another application of the invention, one starts from a flat textile in carbon "cloth" material which is fixed in this configuration by holding it between graphite plates and treated with pyrocarbon. A flat wall is then obtained on which is conferred an elastic return at formation, which is all the more important that the bending radius of the deformed structure is larger. The resulting structure can for example be used for the cartilaginous reinforcement of the auricular wall in veterinary surgery to straighten up dogs' ears.

It will be readily appreciated that the invention has many usefull applications in biology based on the hemocompatibility of carbon: cutaneous or cartilaginous reinforcements, tubular conducts for internal calibration or replacement of blood vessels or any biological conduits, biological valves, etc.

As mentioned before, the invention can also find industrial applications, where elastically flexible articles are needed in a hard environment (high temperatures, corrosive atmosphere, etc.).

As can be seen from the foregoing, the principle of the invention resides in the presence of a thin filim of rough laminar pyrolytic carbon, of thickness generally comprised between 0.2 and 1.5 micron depending on the required flexibility. The treatment is only concerned with the periphery of the elementary carbon fibers but does not affect the interfiber junctions of the initial textile by pyrocarbon bridgings which would risk to rigidify the whole assembly.

It has been found by experimentation that a very low deposition velocity (as low as 1 micron per five hours, for instance) was required to ensure that the deposited pyrolytic carbon was actually of the rough laminar type.

In practice, excellent results have been obtained by carrying out the pyrolytic carbon deposition process in the following conditions.

The starting textile, disposed in its sharping tool, is placed in a treatment chamber brought to a temperature between about 1000° C. and 1100° C. Methane is fed at a rate of between 30 and 40 liters per minute, under a pressure of about 10 mm of mercury (1333 Pa). The length of the treatment depends on the required flexibility. It takes generally a few hours, due to the very low deposition velocity.

The following nonlimiting examples illustrate the process of the present invention.

EXAMPLE 1 Heavy Stiffening

A carbon fibers cloth, woven at 135 g/m2 with roves of 1000 filaments of 8 microns in diameter, was placed between to plane holed plates made of polycrystalline graphite which was previously coated with pyrocarbon.

The whole assembly was placed in a chamber with a circulation of methane at a rate of 35 liters/minute and a pressure of 10 mm. The chamber was heated at 1050° C. for 15 hours.

The thickness of the pyrocarbon film coating each fiber was 1.4 micron.

The microstructure of the film, observed with a optical microscope under polarized light, exhibits a laminar organization of the carbon crystallites, of the rough laminar type.

The elastic behaviour of the "stiffened" cloth was assessed by the winding rigidity on a 20 mm diameter mandrel: it was necessary to exert a bending moment by length unit of $10 \times 10^{-3}$ daN.cm/cm in order to force the plane cloth to be deflected against the barrel. Once the bending moment was suppressed, the cloth straightened up.

EXAMPLE 2 Light Stiffening

A cloth similar to that of example 1 was treated in the same conditions for only 6 hours.

The thickness of the coating was 0.5 micron and its microstructure was still of the rough laminar type.

The winding rigidity was represented by a bending moment by length unit of $0.25 \times 10^{-3}$ daN.cm/cm. Once the bending moment was suppressed, the cloth straightened up.

EXAMPLE 3 No Stiffening

A cloth similar to that of example was treated in the same conditions except that no methane was fed.

No coating was revealed by microscopic observations.

The winding rigidity, assessed on a 20 mm diameter cylinder, was less than the moment due to the own weight of the cloth. The cloth remained bent on the cylinder, without exerting any stress.

What is claimed is:

1. A method for producing an elastically deformable article constituted of a substrate which is elastically deformable with respect to an at rest shape, which comprises:

providing a starting flexible textile substrate formed of a plurality of carbon fibers which textile is capable of being reversibly deformed, imparting to said starting textile a shape corresponding to said at rest shape, treating said starting textile by chemical vapor deposition at a low depositing velocity so as to form around each of said plurality of fibers a thin coating of rough laminar pyrolytic carbon, of a thickness of less than about 1.5 micron, said chemical vapor deposition being carried out so that said carbon fibers are not bonded to one another wherein said article is elastically deformable without breakage of said coating of pyrolytic carbon.

2. A method as claimed in claim 1, wherein said carbon fibers have a diameter comprised between 7 and 10 microns.

3. A method as claimed in claim 1, wherein said chemical vapor deposition of pyrolytic carbon is carried out in a chamber heated at a temperature of between about 1000° C. and 1100° C. and fed with methane.

4. A method as claimed in claim 3, wherein methane is fed at a rate of between about 30 and 40 liters per minute, under a pressure of about 10 mm of mercury.

5. A method as claimed in claim 1, wherein said at rest shape is imparted by means of shaping tools made of graphite coated with pyrolytic carbon.

6. A method as claimed in claim 1, wherein said at rest shape is imparted by means of shaping tools comprising holding plates.

7. A method as claimed in claim 1, wherein said textile is given said at rest shape by way of a seam using a thread which dissolves at high temperature.

8. A method as claimed in claim 1, wherein said textile is a braided sleeve which is compressed axially to give it said at rest shape.

9. A method as claimed in claim 1, wherein said textile used is a braided sleeve which is held axially stretched to give it said at rest shape.

10. A method as claimed in claim 1, wherein said textile is a woven tape which is wound in conical pseudo-spiral to give it said at rest shape.

11. An elastically deformable article constituted of a substrate which is elastically deformable with respect to an at rest shape, said article comprising:

a starting flexible textile formed of a plurality of carbon fibers which textile is capable of being reversibly deformed, said starting textile having a thin coating of rough laminar pyrolytic carbon, of a thickness of less than about 1.5 micron, around each of said plurality of carbon fibers said fibers not being bonded with one another wherein said article can be elastically deformed without breakage of said coating of pyrolytic carbon.

* * * * *